(12) United States Patent
Shaaban et al.

(10) Patent No.: US 11,920,060 B1
(45) Date of Patent: Mar. 5, 2024

(54) MULTIFUNCTIONAL DIORGANYL DISELENIDE TETHERED CELLULOSE AS A CORROSION INHIBITOR OF STAINLESS STEEL

(71) Applicant: KING FAISAL UNIVERSITY, Al-Ahsa (SA)

(72) Inventors: Saad Shaaban, Al-Ahsa (SA); Amr Negm, Al-Ahsa (SA); Hany Mohamed Abd El-Lateef Ahmed, Al-Ahsa (SA); Tarek Ahmed Yousef, Riyadh (SA); Ahmed S. M. Aljanabi, Tikrit (IQ)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/236,016

(22) Filed: Aug. 21, 2023

(51) Int. Cl.
*C09D 5/08* (2006.01)
*C07C 391/02* (2006.01)
*C09D 101/02* (2006.01)

(52) U.S. Cl.
CPC ............ *C09D 5/086* (2013.01); *C07C 391/02* (2013.01); *C09D 101/02* (2013.01)

(58) Field of Classification Search
CPC .................................................. C07C 319/02
See application file for complete search history.

(56) References Cited

U.S. PATENT DOCUMENTS

| | | | | |
|---|---|---|---|---|
| 3,965,049 A | * | 6/1976 | Grushkin | G03G 5/07 430/80 |
| 4,613,468 A | * | 9/1986 | Sandman | C07C 395/00 562/899 |
| 5,973,009 A | * | 10/1999 | Tailhan-Lomont | C07D 233/66 514/706 |
| 9,593,142 B2 | * | 3/2017 | Arora | C07K 5/0808 |
| 2008/0015189 A1 | * | 1/2008 | Hamblin | A61P 31/00 544/31 |
| 2014/0155641 A1 | | 6/2014 | Hanes | |
| 2015/0232504 A1 | * | 8/2015 | Arora | C07D 209/20 530/331 |
| 2017/0027168 A1 | | 2/2017 | Heath | |
| 2019/0010591 A1 | * | 1/2019 | Das | C22F 1/047 |

OTHER PUBLICATIONS

Abd El-Lateef et al. (Colloids and Surfaces A: Physicochemical and Engineering Aspects 625 (2021) 126894) (Year: 2021).*
Le, et al., "Covalent Grafting of Chitosan onto Stainless Steel Through Aryldiazonium Self-Adhesive Layers.", Applied Materials & Interfaces, 2014, 6(12), 9085-9092.
El-Askalany, et al., "Novel Tetrazole-Based Symmetrical Diselenides as Corrosion Inhibitors for N80 Carbon Steel in 1 M HCL Solutions: Experimental and Theoretical Studies.", Journal of Molecular Liquids, vol. 223, Nov. 2016, pp. 497-508.
Al Kiey, et al., "Potential Anticorrosive Performance of Green and Sustainable Inhibitor Based on Cellulose Derivatives for Carbon Steel", Journal of Molecular Liquids, vol. 338, Sep. 15, 2021, 116604.

* cited by examiner

*Primary Examiner* — Liam J Heincer

(74) *Attorney, Agent, or Firm* — Nath, Goldberg & Meyer; Richard C. Litman

(57) ABSTRACT

New diorganyl diselenide compounds are described herein, as well as the use of such diorganyl diselenide compounds in forming anticorrosion coatings for stainless steel. Also described are methods for forming the new diorganyl diselenide compounds as well as anti-corrosion coatings containing the diorganyl diselenide compounds.

20 Claims, 1 Drawing Sheet

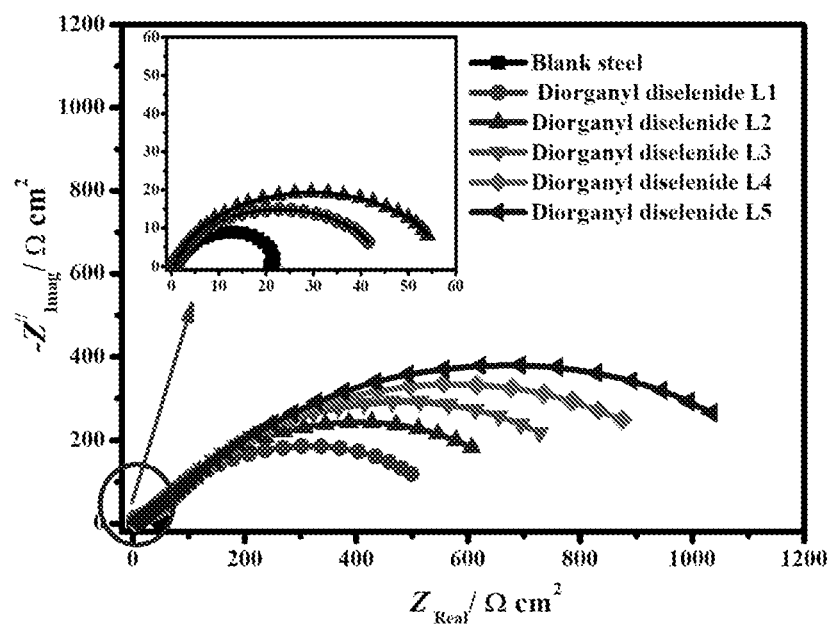

MULTIFUNCTIONAL DIORGANYL DISELENIDE TETHERED CELLULOSE AS A CORROSION INHIBITOR OF STAINLESS STEEL

BACKGROUND

1. Field

The disclosure of the present patent application relates to novel diselenide compounds and the use of the same for inhibiting corrosion in stainless steel.

2. Description of the Related Art

Corrosion is a loss of material due to physical, chemical, electro-chemical or biological reaction with the environment. The use of anti-corrosive coatings and linings has become a necessity to safeguard huge investments in terms of money and property. The demand for efficient anti-corrosion coatings is continuously increasing. The anti-corrosive coatings should protect metal surfaces from degradation due to air and moisture oxidation, prevent direct contact of environmental chemical hazards, act as a barrier from corrosive materials, prolong their structural life and efficiency.

Classical corrosion inhibitors (e.g., organics and inorganics) have shown good inhibition effects. However, their application is limited by their toxicity, high cost, non-degradability, insufficient surface protection, and instability under harsh conditions. On the other hand, green corrosion inhibitors (e.g., surfactant, ionic liquid, natural, and bio-extracts) have attracted the attention of researchers owing to their harmless nature, low-cost, biodegradability, and stability.

In this context, cellulose is commonly found in nature and is considered as a green recyclable biopolymer with a cheap production cost. Cellulose is a polysaccharide with a linear nature composed of glucose units combined via ß-1,4-glycosidic linkage. It is the most abundant all-natural biopolymer on earth and is produced in $7.5 \times 10^{10}$ tons yearly. Interestingly, its special molecular structure and physiological properties cause its unique absorbability and degradability, making cellulose an ideal eco-friendly corrosion inhibitor.

Cellulose-based inhibitors can function well at room temperature and at dilute acid concentration; however, they cannot withstand harsh conditions i.e., high temperature and concentrated acid (>15 wt % HCl).

Therefore, developing novel cellulose-based inhibitors solving the aforementioned problems are highly desired in stainless steel pipeline cleaning solutions and acidizing fluids, as well as in the petrochemical industries.

SUMMARY

The present subject matter relates to the protection of stainless steel against corrosion using diorganyl diselenide tethered cellulose. Described herein are products and methods for corrosion protection of stainless steel with eco-friendly, less expensive diorganyl diselenide tethered cellulose inhibitors. Accordingly, various aspects of the present subject matter relate to the grafting of diorganyl diselenides on the surface of the steel employing the GraftFast™ process (diazonium-induced anchoring process), which in turn can form a self-adhesive layer through the diorganyl diselenide diazonium layers. The grafted diorganyl diselenides can be converted to the corresponding bis-diazonium seed layer by immersion in an acidic $NaNO_2$ solution. The latter can be used as a self-adhesive surface for subsequent spontaneous coating of cellulose on the steel surface.

In an embodiment, the present subject matter relates to a compound of the formula I:

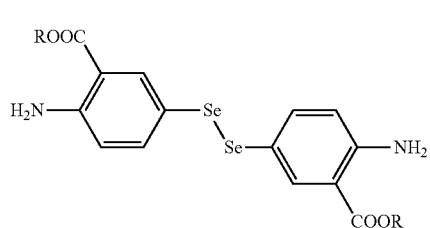

wherein:
R is $CH_3$, $CH_2CH$, $CH_2CH_2CH_3$, or $CH(CH_3)_2$;
or a diazonium salt thereof.

In another embodiment, the present subject matter relates to an anticorrosion coating comprising the diorganyl diselenide compounds described herein.

In a further embodiment, the present subject matter relates to a method of preventing corrosion in a material, the method comprising:
grafting the anticorrosion coating as described herein on a surface of a material to form a self-adhesive diorganyl diselenide layer on the material, wherein the material is selected from the group consisting of steel, iron, copper, and a combination thereof.

In an additional embodiment, the present subject matter relates to a method of making the diorganyl diselenide compound as described herein, the method comprising:
dissolving a selenocyanate in ethanol to obtain a first solution;
adding sodium hydroxide to the first solution to obtain a reaction mixture;
stirring the reaction mixture at room temperature to obtain a stirred reaction mixture;
adding ice-cold water to the stirred reaction mixture to obtain a precipitate; and
filtering the precipitate to obtain the diorganyl diselenide compound.

These and other features of the present subject matter will become readily apparent upon further review of the following specification.

BRIEF DESCRIPTION OF DRAWINGS

FIG. 1 is a Nyquist plot for pristine steel specimens and coated by diorganyl diselenide films with different layers in an acidic chloride medium at 30° C.

Similar reference characters denote corresponding features consistently throughout the attached drawings.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the protection of stainless steel against corrosion using diorganyl diselenide tethered cellulose. Described herein are products and methods for corrosion protection of stainless steel with eco-friendly, less expensive diorganyl diselenide tethered cellulose corrosion inhibitors. Accordingly, various aspects of the present subject matter relate to the grafting of diorganyl diselenides on the surface of the steel employing the GraftFast™ process (diazonium-induced anchoring process), which in turn can form a self-adhesive layer through the diorganyl diselenide diazonium layers. The grafted diorganyl diselenides can be converted to the corresponding bis-diazonium seed layer by immersion in an acidic $NaNO_2$ solution. The latter can be used as a self-adhesive surface for subsequent spontaneous coating of cellulose on the steel surface.

In an embodiment, the present subject matter relates to a compound of the formula I:

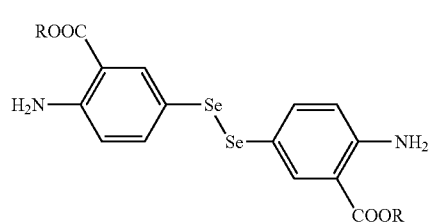

wherein:
R is $CH_3$, $CH_2CH_3$, $CH_2CH_2CH_3$, or $CH(CH_3)_2$;
or a diazonium salt thereof.

In an embodiment, the compound can be selected from the group consisting of:
dipropyl 5,5'-diselanediylbis(2-aminobenzoate) (4a);
diisopropyl 5,5'-diselanediylbis(2-aminobenzoate) (4b);
and a diazonium salt thereof.

In another embodiment, the present subject matter relates to an anticorrosion coating comprising the diorganyl diselenide compounds described herein.

In certain embodiments, the diorganyl diselenide compound can be grafted on a surface of a material to form a self-adhesive diorganyl diselenide layer on the material, wherein the material can be selected from the group consisting of steel, iron, copper, and a combination thereof. In an embodiment, the material can be stainless steel. The grafting of the diorganyl diselenides on the surface of, e.g., stainless steel, can be observed by referring to the following Scheme 1:

Scheme 1

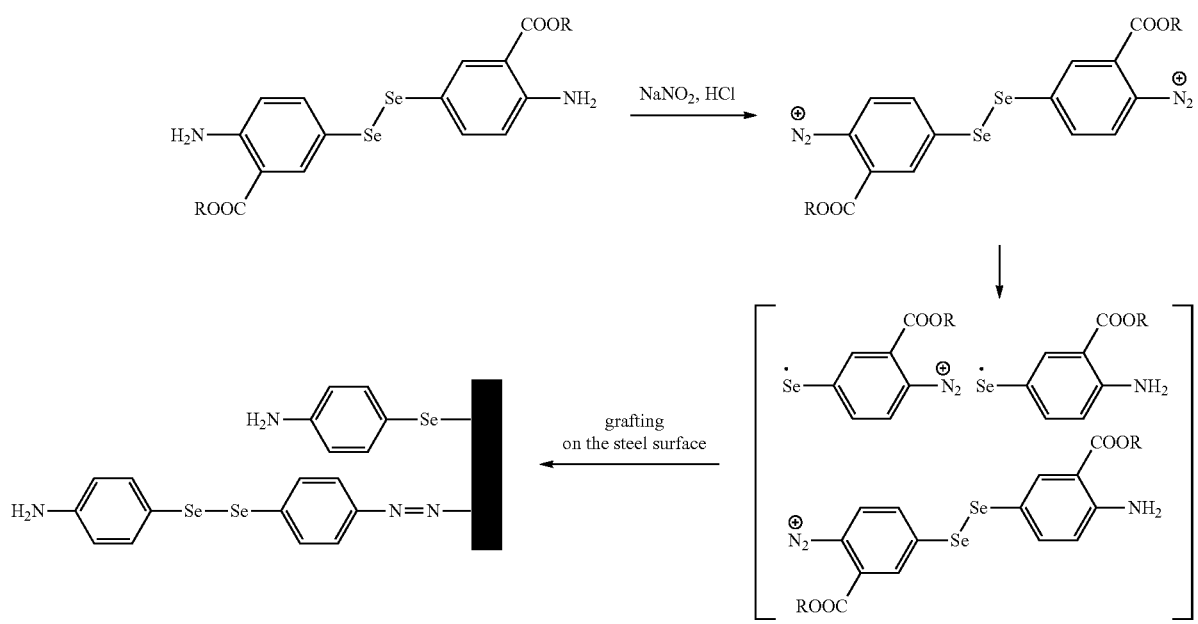

In another embodiment, the self-adhesive diorganyl diselenide layer can comprise diorganyl diselenide diazonium. That is, the self-adhesive diorganyl diselenide layer can comprise the diorganyl diselenide compound, the diorganyl diselenide diazonium, or a combination thereof.

In a further embodiment, cellulose can be coated on the self-adhesive diorganyl diselenide layer. This cellulose coating can be observed by referring to the following Scheme 2:

Scheme 2

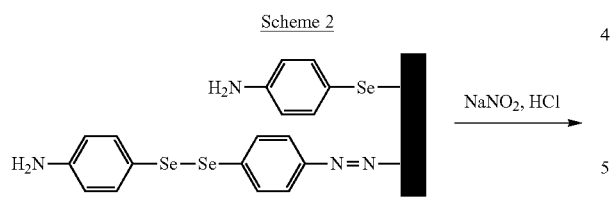

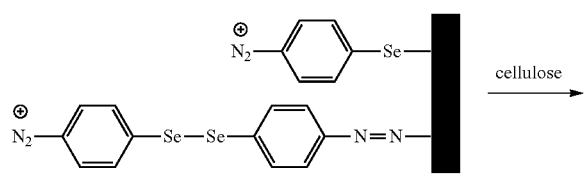

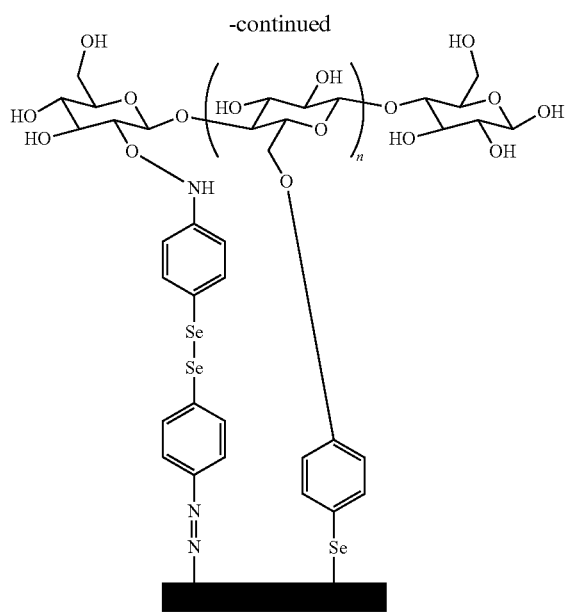

In an embodiment, one to five layers of the self-adhesive diorganyl diselenide layer are formed on the material. In this regard, in one embodiment, one layer of the self-adhesive diorganyl diselenide layer can be formed on the material and the anticorrosion coating having a thickness of about 1.05 μm to about 1.39 μm, or about 1.22 μm. In another embodiment, five layers of the self-adhesive diorganyl diselenide layer can be formed on the material and the anticorrosion coating having a thickness of about 4.55 μm to about 5.37 μm, or about 4.96 μm. In an embodiment, the denser film with five layers can provide superior protection against steel corrosion. As the number of diorganyl diselenide film layers increases, the obstruction effect of the coating films against corrosive ions can be enhanced, preventing contact of a corrosive material with the steel surface.

In another embodiment, the anticorrosion coating can be formed as a homogenous film.

In an additional embodiment, polarization resistance of the self-adhesive diorganyl diselenide layer on the material can increase by about 10 to about 28 times a polarization resistance of the material without the self-adhesive diorganyl diselenide layer. In this regard, 1, 2, 3, 4, and 5 layers of diorganyl diselenide film coatings can result in polarization resistance (Rp) values that are 10.5, 12.4, 17.8, 22.4, and 28.3 times larger, respectively, than that of an uncoated steel substrate having a Rp=55.91 $\Omega cm^2$. This increase in polarization resistance can be attributed to the formation of a protective coating film on the steel surface and its barrier properties. In an embodiment, the Rp values of the steel substrate coated with five layers of diorganyl diselenide films can be greater than those with only one layer, indicating a more effective barrier against corrosive ions due to the compacted structure.

In a further embodiment, the present subject matter relates to a method of preventing corrosion in a material, the method comprising:

grafting the anticorrosion coating as described herein on a surface of a material to form a self-adhesive diorganyl diselenide layer on the material, wherein the material is selected from the group consisting of steel, iron, copper, and a combination thereof. In certain embodiments, the material can be stainless steel.

In an embodiment, the methods of preventing corrosion in a material can further comprising immersing the self-adhesive diorganyl diselenide layer on the material in an acidic $NaNO_2$ solution; and coating cellulose on the diorganyl diselenide layer.

In an additional embodiment, the present subject matter relates to a method of making the diorganyl diselenide compound as described herein, the method comprising:

dissolving a selenocyanate in ethanol to obtain a first solution;

adding sodium hydroxide to the first solution to obtain a reaction mixture;

stirring the reaction mixture at room temperature to obtain a stirred reaction mixture;

adding ice-cold water to the stirred reaction mixture to obtain a precipitate; and filtering the precipitate to obtain the diorganyl diselenide compound.

This process can be further summarized according to the following Scheme 3:

Scheme 3

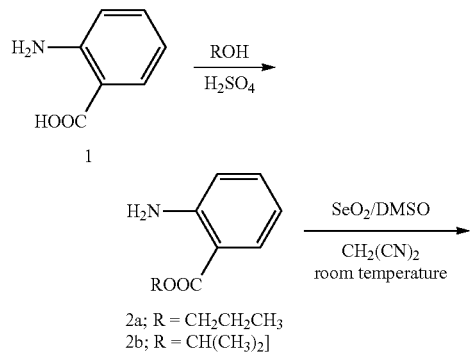

2a; R = CH$_2$CH$_2$CH$_3$
2b; R = CH(CH$_3$)$_2$]

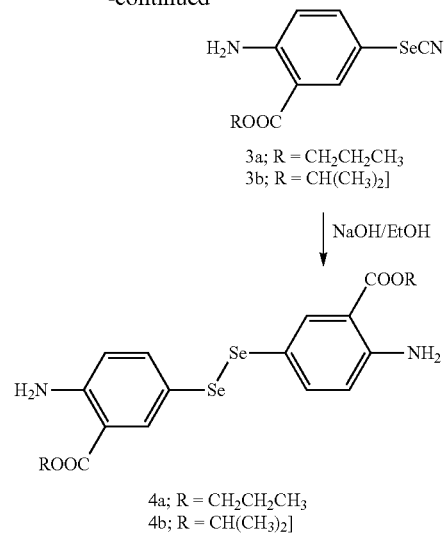

3a; R = CH$_2$CH$_2$CH$_3$
3b; R = CH(CH$_3$)$_2$]

4a; R = CH$_2$CH$_2$CH$_3$
4b; R = CH(CH$_3$)$_2$]

In a further embodiment, the selenocyanate used in the production methods can be selected from the group consisting of propyl 2-amino-5-selenocyanatobenzoate (3a) and isopropyl 2-amino-5-selenocyanatobenzoate (3b).

In another embodiment of the present methods, the stirring can be conducted for at least about 2 hours. Further, the selenocyanate and the sodium hydroxide can be used in an about 1:1 molar ratio.

In an additional embodiment, the present compound production methods can further comprise dissolving the diorganyl diselenide compound in aqueous HCl to obtain a second solution;

cooling the second solution to a temperature of about 0 to about 5° C.;

adding $NaNO_2$ to the second solution while maintaining the temperature at about 0 to about 5° C.; and obtaining the diazonium salt of the diorganyl diselenide compound.

In an embodiment, the diorganyl diselenide compound and the $NaNO_2$ can be used in an about 1:2.2 molar ratio.

The present teachings are illustrated by the following examples.

EXAMPLES

Example 1

Preparation of propyl 2-aminobenzoate (2a) and isopropyl 2-aminobenzoate (2b) (Scheme 3)

Propyl 2-aminobenzoate (2a) and isopropyl 2-aminobenzoate (2b) were synthesized from the acid catalyzed esterification of 2-aminobenzoic acid using excess propyl and isopropyl alcohol in $H_2SO_4$, respectively.

Example 2

Preparation of propyl 2-amino-5-selenocyanatobenzoate (3a) and isopropyl 2-amino-5-selenocyanatobenzoate (3b) (Scheme 3)

Propyl 2-amino-5-selenocyanatobenzoate (3a) and isopropyl 2-amino-5-selenocyanatobenzoate (3b) were prepared from the reaction of 2a and 2b with triselenium dicyanide prepared in situ from malononitrile and selenium dioxide in DMSO as follow: $SeO_2$ (3 mmol) was added to $CH_2(CN)_2$ (1.5 mmol) in DMSO (5 mL). The solution was stirred for 30 min at room temperature. Unreacted selenium was removed by filtration. After that, 2a or 2b (1.25 mmol) were then added, and the reaction mixture was stirred for a further 2 hours at room temperature, respectively. Cold water was added to terminate the reaction, and the formed precipitate was filtered, washed several times with water and $Na_2CO_3$ solution, and dried.

Example 3

Preparation of diselenides dipropyl 5,5'-diselanediylbis(2-aminobenzoate) (4a) and diisopropyl 5,5'-diselanediylbis(2-aminobenzoate) (4b) (Scheme 3)

Diselenides dipropyl 5,5'-diselanediylbis(2-aminobenzoate) (4a) and diisopropyl 5,5'-diselanediylbis(2-aminobenzoate) (4b) were synthesized from the reaction of 3a or 3b with sodium hydroxide in ethanol as follow: Selenocyanates 3a or 3b (8 mmol) were dissolved in EtOH (40 mL), and then sodium hydroxide (8 mmol) was added, respectively. The reaction mixture was stirred for 2 h at room temperature, and ice-cold water was then added, and the resulting precipitate was filtered, washed several times with water.

Example 3

Preparation of diselenides dipropyl 5,5'-diselanediylbis(2-aminobenzoate) (4a) and diisopropyl 5,5'-diselanediylbis(2-aminobenzoate) (4b) diazonium salts Diselenides 4a or 4b (2 mmol) were dissolved in aqueous HCl (4 mL) and cooled to 0-5° C. $NaNO_2$ (4.4 mmol, in 10 mL water) was then added to the previously prepared solution while maintaining the temperature at 0-5° C.

Example 4

EIS Studies

The EIS technique was used to investigate the protective properties of diorganyl diselenide films on steel specimens coated with different layers of the compound in a 3.5% NaCl solution containing 1.0 M HCl at 30° C. FIG. 1 shows the Nyquist profiles of the pristine steel specimens and the coated specimens with varying layers of diorganyl diselenide in an acidic chloride medium at 30° C.

For the uncoated steel specimens, the profile exhibited a single capacitive loop (one semicircle), which is indicative of the charge transfer associated with the corrosion process. However, for the coated AISI-SS specimens with one to five layers of diorganyl diselenide, two half-circles were observed. At higher frequency (GF) regions, the inductive loop can be attributed to the resistance of the coating (Rc) and the capacitance of the coating layer (CPEcoat, Qcoat). At lower frequency (SF) regions, the capacitive loop can be attributed to the capacitance of the double layer (Qdl, CPEdl) in parallel with the polarization resistance (Rp). The presence of two semicircles in the case of coated layers has been noted. However, the capacitive loops are not perfect semicircles and are somewhat depressed. This is due to the frequency dispersion effect caused by the roughness and inhomogeneity of the steel surface. It was observed from FIG. 1 the impedance value of all covered steel substrates is greater than that of the pristine bar, and the value of resistance rises with growing the layer thickness (layers number). This designated that the corrosion rate declined in the existence of diorganyl diselenide films coating films and continues to shrink by growing the thickness of the layers.

According to Table 1, below, the polarization resistance (Rp) values of the diorganyl diselenide-coated steel samples increased significantly compared to the pristine steel samples (Rp=55.91 $\Omega cm^2$). With 1, 2, 3, 4, and 5 layers of diorganyl diselenide film coatings, the values of Rp were 10.5, 12.4, 17.8, 22.4, and 28.3 times larger than that of the uncoated steel substrate. This increase in polarization resistance can be attributed to the formation of a protective coating film on the steel surface and its barrier properties.

Moreover, the Rp values of the steel substrate coated with five layers of diorganyl diselenide films were greater than those with only one layer, indicating a more effective barrier against corrosive ions due to the compacted structure.

TABLE 1

EIS parameters for uncoated AISI-SS and coated by diorganyl diselenide films with different layers in 3.5% NaCl + 1.0M HCl solution at 30° C.

| Samples Description | $R_s$/ $\Omega$ $cm^2$ ± SD | $R_p$/ $\Omega$ $cm^2$ | PC/ % |
|---|---|---|---|
| Pristine steel | 2.02 | 55.91 | — |
| Diorganyl diselenide L1 | 3.16 | 618.87 | 90.983 |
| Diorganyl diselenide L2 | 3.27 | 725.445 | 92.308 |
| Diorganyl diselenide L3 | 3.64 | 1032.675 | 94.596 |
| Diorganyl diselenide L4 | 5.21 | 1292.865 | 95.684 |
| Diorganyl diselenide L5 | 8.34 | 1838.315 | 98.102 |

The protective capacity of the investigated coating films was studied with regard to their thickness and roughness. The one-layer film-coated specimen had a thickness of 1.22±0.17 μm while reiterating the coating procedure with five layers resulted in thicknesses of up to 4.96±0.41 μm. The denser film with five layers provided superior protection against steel corrosion. As the number of diorganyl diselenide film layers increased, the obstruction effect of the coating films against corrosive ions was enhanced, preventing contact with the steel surface.

The roughness indicator (Ra) for the coated substrates with one and five layers was found to be 0.053±0.12 μm and 0.012 μm, respectively, indicating a good homogeneity of the surface of the diorganyl diselenide films.

It is to be understood that the compounds, coatings, and methods are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound of the formula I:

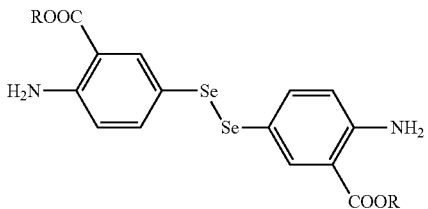

wherein:
R is $CH_3$, $CH_2CH_3$, $CH_2CH_2CH_3$, or $CH(CH_3)_2$;
or a diazonium salt thereof.

2. The compound of claim 1, wherein the compound is selected from the group consisting of:
dipropyl 5,5'-diselanediylbis(2-aminobenzoate) (4a);
diisopropyl 5,5'-diselanediylbis(2-aminobenzoate) (4b);
and a diazonium salt thereof.

3. An anticorrosion coating comprising the compound of claim 1.

4. The anticorrosion coating of claim 3, wherein the compound is grafted on a surface of a material to form a self-adhesive diorganyl diselenide layer on the material, wherein the material is selected from the group consisting of steel, iron, copper, and a combination thereof.

5. The anticorrosion coating of claim 4, wherein the material is stainless steel.

6. The anticorrosion coating of claim 4, wherein the self-adhesive diorganyl diselenide layer comprises diorganyl diselenide diazonium.

7. The anticorrosion coating of claim 4, wherein cellulose is coated on the self-adhesive diorganyl diselenide layer.

8. The anticorrosion coating of claim 4, wherein one to five layers of the self-adhesive diorganyl diselenide layer are formed on the material.

9. The anticorrosion coating of claim 8, wherein one layer of the self-adhesive diorganyl diselenide layer is formed on the material and the anticorrosion coating has a thickness of about 1.05 μm to about 1.39 μm.

10. The anticorrosion coating of claim 8, wherein five layers of the self-adhesive diorganyl diselenide layer are formed on the material and the anticorrosion coating has a thickness of about 4.55 μm to about 5.37 μm.

11. The anticorrosion coating of claim 4, wherein the anticorrosion coating is formed as a homogenous film.

12. The anticorrosion coating of claim 8, wherein polarization resistance of the self-adhesive diorganyl diselenide layer on the material increased by about 10 to about 28 times a polarization resistance of the material without the self-adhesive diorganyl diselenide layer.

13. A method of preventing corrosion in a material, the method comprising:
grafting the anticorrosion coating of claim 3 on a surface of a material to form a self-adhesive diorganyl diselenide layer on the material, wherein the material is selected from the group consisting of steel, iron, copper, and a combination thereof.

14. The method of claim 13, further comprising immersing the self-adhesive diorganyl diselenide layer on the material in an acidic $NaNO_2$ solution; and
coating cellulose on the diorganyl diselenide layer.

15. A method of making the compound of claim 1, the method comprising:
dissolving a selenocyanate in ethanol to obtain a first solution;
adding sodium hydroxide to the first solution to obtain a reaction mixture;
stirring the reaction mixture at room temperature to obtain a stirred reaction mixture;
adding ice-cold water to the stirred reaction mixture to obtain a precipitate; and
filtering the precipitate to obtain the compound of claim 1.

16. The method of claim 15, wherein the selenocyanate is selected from the group consisting of propyl 2-amino-5-selenocyanatobenzoate (3a) and isopropyl 2-amino-5-selenocyanatobenzoate (3b).

17. The method of claim 15, wherein the stirring is conducted for at least about 2 hours.

18. The method of claim 15, wherein the selenocyanate and the sodium hydroxide are used in an about 1:1 molar ratio.

19. The method of claim 15, further comprising dissolving the compound in aqueous HCl to obtain a second solution;
cooling the second solution to a temperature of about 0 to about 5° C.;
adding $NaNO_2$ to the second solution while maintaining the temperature at about 0 to about 5° C.; and
obtaining the diazonium salt of the compound.

20. The method of claim 19, wherein the compound and the $NaNO_2$ are used in an about 1:2.2 molar ratio.

* * * * *